United States Patent [19]

Whitsell

[11] Patent Number: Plant 5,309

[45] Date of Patent: Oct. 30, 1984

[54] AVOCADO TREE—"ESTHER"

[75] Inventor: Robert H. Whitsell, Riverside, Calif.

[73] Assignee: The Regents of the University of California, Berkeley, Calif.

[21] Appl. No.: 467,716

[22] Filed: Feb. 18, 1983

[51] Int. Cl.[3] ..... A01H 5/03

[52] U.S. Cl. ..... Plt./44

[58] Field of Search ..... Plt./44

*Primary Examiner*—Robert E. Bagwill

*Attorney, Agent, or Firm*—Townsend and Townsend

[57] ABSTRACT

A new and distinct variety of avocado tree characterized by its high productivity (about twice that of 'Hass') and its late bearing season (from about August into December) and further characterized by its tree growth which is only about two-thirds the size of 'Hass' and is rounded and quite uniform in outline.

2 Drawing Figures

DESCRIPTION

This invention relates to a new and distinct variety of avocado tree designated as 'Esther' and tested as selection NB67.

'Esther' is a hybrid of a 'Nabal'-self×a 'Hass'-"grandchild".

'Esther' has been propagated asexually by T-budding, whip-grafting, saddle-grafting and saw-kerf grafting at the University of California, Riverside and South Coast Field Station facilities in Southern California where the variety has been tested.

Figure 1:
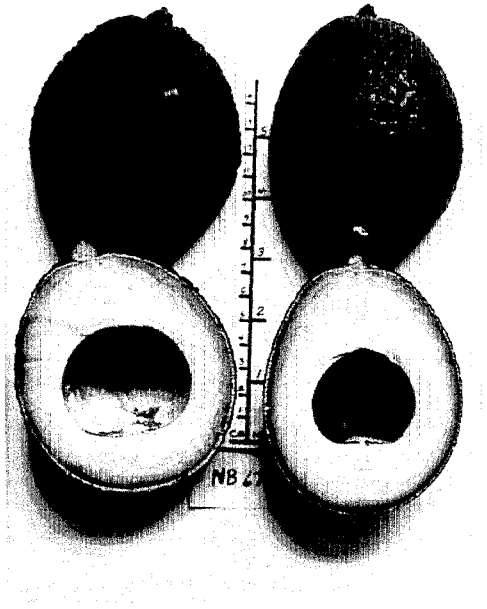
FIG. 1 shows typical fruiting characteristics of the tree.
Figure 2:
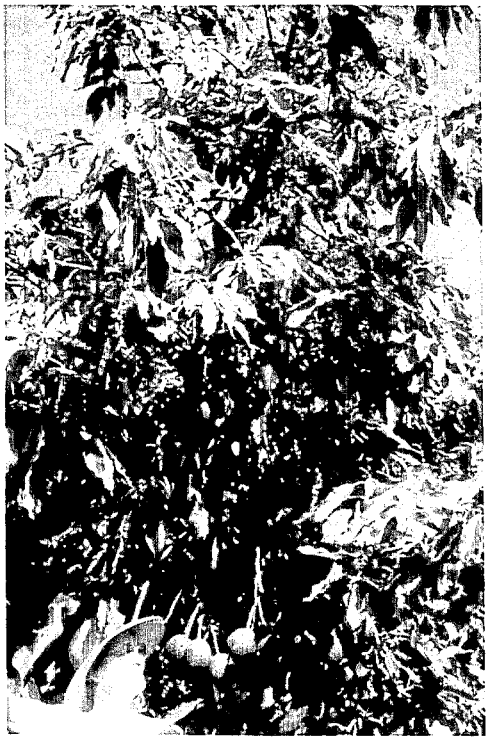
FIG. 2 shows the heavy fruit-set ability typical of the tree.

'Esther' has two primary distinguishing characteristics. It is highly productive in that it will out-bear 'Hass' by about two to one. Also 'Esther' has a very late season, hanging about three months after the 'Hass' harvest has been largely depleted. Because of its high productivity and late season 'Esther' fills a long felt want for a good fall avocado when the fall season is otherwise dominated by mediocre thin-skinned varieties.

No resistance of 'Esther' is known to the few insects which are rarely a problem to avocado trees, nor to Verticillium wilt, the Black-streak disease or the Sunblotch viroid. Resistance to Phytophthora is a property of the rootstock and not the scion top. In resistance to the physiological disease of freezing injury, 'Esther' rates "tender" and is about comparable to the 'Hass' standard.

It is impossible to assign very meaningful distinctions of the new variety based upon color. With reference to the Horticulture Colour Charts (issued by Wilson Colour Ltd. in collaboration with The Royal Horticultural Society) typical fruit of 'Esther' has the background skin color designated as Parsley Green, oo962 (Repertoire, Vert barbedienne 287/1). The basic green skin color not only varies of itself, but is flecked with numerous tiny islands of varying yellowish shades. Moreover, the two halves of the fruit usually differ in average color. Each average color differs according to the time of fruit-set (which may vary widely on a tree), the degree of maturity, geographic location, and possibly other factors. Nevertheless, the basic background skin color above-identified is the most consistent color feature of the fruit of this variety.

TREES AND FOLIAGE

'Esther', as in the case of most avocado cultivars, does not have distinctive foliage and cannot consistently be distinguished from 'Hass' on the basis of leaf, flower, or limb traits. In tree form 'Esther' is rounded and quite uniform in tree outline. Growth is vigorous, but only about two-thirds the size of 'Hass'. Its smaller tree size is a distinct economic advantage.

FRUIT

The fruit of 'Esther' is quite distinctive from all other avocado cultivars. It is very thick and weighs about 300 grams. It has moderate to coarse roughness and some russeting. Flesh color is about like 'Hass', and it is not as richly flavored as 'Hass'. Seed is larger than 'Hass'. Production is consistently heavy with exceptionally little alternation. The season is about August into December.

I claim:

1. The new and distinct variety of avocado tree herein described and illustrated and identified by the characteristics enumerated above.

* * * * *